United States Patent
Lautenschlaeger (10) Patent No.: US 10,856,206 B2
(45) Date of Patent: Dec. 1, 2020

(54) METHOD FOR PROVIDING IMAGE DATA TO A CENTRAL UNIT

(71) Applicant: Siemens Healthcare GmbH, Erlangen (DE)

(72) Inventor: Stefan Lautenschlaeger, Nuremberg (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 0 days.

(21) Appl. No.: 16/228,939

(22) Filed: Dec. 21, 2018

(65) Prior Publication Data

US 2019/0200274 A1  Jun. 27, 2019

(30) Foreign Application Priority Data

Dec. 27, 2017  (EP) ..................................... 17210728

(51) Int. Cl.
*H04W 24/00* (2009.01)
*H04W 40/20* (2009.01)
(Continued)

(52) U.S. Cl.
CPC ............. *H04W 40/20* (2013.01); *A61B 6/032* (2013.01); *A61B 6/4405* (2013.01); *A61B 6/563* (2013.01); *G08G 1/096827* (2013.01); *G08G 1/096855* (2013.01); *G16H 30/20* (2018.01); *H04W 4/024* (2018.02); *H04W 4/029* (2018.02); *H04W 4/44* (2018.02)

(58) Field of Classification Search
CPC ....... H04W 4/029; H04W 64/00; H04W 4/02; H04W 28/16; H04W 28/26; H04W 88/06
See application file for complete search history.

(56) References Cited

U.S. PATENT DOCUMENTS

| 9,432,929 | B1 * | 8/2016 | Ross | .................... H04W 4/026 |
| 2003/0103086 | A1 * | 6/2003 | Robinson | ................ H04W 4/02 |
| | | | | 715/810 |

(Continued)

OTHER PUBLICATIONS

Extended European Search Report for European Application No. 17210728.8 Published May 22, 2018.
(Continued)

*Primary Examiner* — Shantell L Heiber
(74) *Attorney, Agent, or Firm* — Harness, Dickey & Pierce, P.L.C.

(57) ABSTRACT

A method is disclosed for providing image data to a central unit. In an embodiment, the method includes acquiring image data using a mobile imaging device, the mobile imaging device being a mobile communication device or being connected to a mobile communication device; determining bandwidth information relating to a locally available bandwidth for a radio network or multiple separate radio networks; at least one of selecting a communication location for the mobile communication device based on the bandwidth information determined, and selecting the radio network or multiple separate radio networks based on the bandwidth information determined; and at least one of moving the mobile communication device to the selected communication location selected, and using the radio network or multiple separate radio networks selected to transfer the image data to the central unit.

19 Claims, 1 Drawing Sheet

(51) Int. Cl.
*G08G 1/0968* (2006.01)
*H04W 4/024* (2018.01)
*A61B 6/00* (2006.01)
*H04W 4/44* (2018.01)
*G16H 30/20* (2018.01)
*A61B 6/03* (2006.01)
*H04W 4/029* (2018.01)

(56) References Cited

U.S. PATENT DOCUMENTS

| | | | |
|---|---|---|---|
| 2003/0220835 A1* | 11/2003 | Barnes, Jr. | G06Q 10/1053 705/14.36 |
| 2006/0209891 A1* | 9/2006 | Yamada | H04L 45/00 370/468 |
| 2008/0188228 A1* | 8/2008 | Pecen | H04W 48/18 455/449 |
| 2008/0268855 A1 | 10/2008 | Hanuni et al. | |
| 2008/0270379 A1* | 10/2008 | Ramakrishna | G06F 9/383 |
| 2012/0066366 A1 | 3/2012 | Blaisdell | |
| 2013/0003756 A1 | 1/2013 | Mitchell et al. | |
| 2013/0024107 A1* | 1/2013 | Xie | G01C 21/3461 701/423 |
| 2014/0244301 A1* | 8/2014 | Lee | G06F 19/3418 705/3 |
| 2014/0257695 A1* | 9/2014 | Annapureddy | G08G 1/096811 701/537 |
| 2014/0307636 A1 | 10/2014 | Lin | |
| 2014/0344658 A1* | 11/2014 | Srinivasan | G06F 17/2235 715/205 |
| 2015/0146697 A1 | 5/2015 | Gibbon et al. | |
| 2015/0149591 A1* | 5/2015 | Gibbon | H04L 67/325 709/219 |
| 2016/0174271 A1* | 6/2016 | Jeong | H04W 68/12 455/445 |
| 2016/0191973 A1* | 6/2016 | Joy | H04N 21/26216 725/75 |
| 2017/0300654 A1 | 10/2017 | Stein et al. | |

OTHER PUBLICATIONS

Office Action for European Patent Application No. 17210728.6 dated Mar. 23, 2020.

* cited by examiner

METHOD FOR PROVIDING IMAGE DATA TO A CENTRAL UNIT

PRIORITY STATEMENT

The present application hereby claims priority under 35 U.S.C. § 119 to European patent application number EP17210728.6 filed Dec. 27, 2017, the entire contents of which are hereby incorporated herein by reference.

FIELD

Embodiments of the invention generally relate to a method for providing image data to a central unit; a vehicle, especially an ambulance; a computer program; and/or a computer-readable storage medium.

BACKGROUND

When treating patients that suffered a stroke, it is highly relevant for the success of the treatment to start the treatment as early as possible. Thrombolysis treatment to brake down blood clots can in principle be already started in an ambulance while the patient is transported to a hospital for the treatment. Before the treatment can be started it should however be ensured that patient is actually suffering from a stroke. E.g. a cerebral haemorrhage can cause similar symptoms and a thrombolysis treatment would potentially worsen such conditions. It is therefore advantageous to already perform a certain amount of diagnosis on a patient, while the patient is still be transported to a hospital.

Relatively new devices that allow for such an early diagnosis are so called mobile stroke units. Those comprise of an ambulance equipped with a computed tomography scanner that gets dispatched to the place at which the potential stroke has occurred. Besides other tests, one or multiple CT-scans are acquired on the scene. Since it is typically not possible to have specialists, e.g. neuro radiologists, riding with each such ambulance, the acquired image data is typically transmitted back to a central unit, e.g. at a hospital, and diagnosis is performed there. Therefore telemedicine is performed.

The speed of the data transfer depends on the bandwidth of the mobile data connection at the current location of the ambulance. In some spots the transfer speed of the available cellular network will be very slow, which results in a prolonged data transfer. In the worst case the data transfer cannot be done in a reasonable timeframe, forcing the ambulance personal to bring the patient to the hospital without the benefit of an early treatment.

The above problems limit the effective use of mobile stroke units to cities or other areas with a high cellular network coverage. To avoid these problems, it would be necessary to have e.g. a neuro radiologist riding with the mobile stroke unit or to use high cost means for data transfer, e.g. a dedicated satellite connection. Those approaches would noticeably increase the cost of operating a mobile stroke unit, thereby decreasing the degree of usage.

SUMMARY

At least one embodiment of the invention provides an improved method for providing image data to a central unit that can especially improve the data transfer from a mobile stroke unit to a hospital.

At least one embodiment of the invention provides for a method of providing image data to a central unit, comprising:
 acquiring image data using a mobile imaging device, especially a mobile medical imaging device, that comprises or is connected to a mobile communication device,
 determining a bandwidth information that relates to a locally available bandwidth for a radio network or multiple separate radio networks, especially cellular networks,
 selecting a communication location for the mobile communication device (8) and/or selecting at least one of the radio networks based on the bandwidth information, and
 moving the mobile communication device to the selected communication location and/or using the selected radio network to transfer the image data to the central unit.

In addition to the inventive method, at least one embodiment of the invention concerns a vehicle, especially an ambulance, comprising an imaging device, especially a medical imaging device, and a communication device, wherein the vehicle is configured to perform at least one embodiment of the inventive method. The vehicle can especially be a mobile stroke unit.

At least one embodiment of the invention concerns a vehicle, comprising:
 a mobile imaging device to acquire image data, the mobile imaging device being a mobile communication device or being connected to a mobile communication device; and
 a communication device, configured to
  determine bandwidth information relating to a locally available bandwidth for a radio network or multiple separate radio networks;
 at least one of
  select a communication location for the mobile communication device based on the bandwidth information determined, and
  select the radio network or multiple separate radio networks based on the bandwidth information determined; and
 at least one of
  move the mobile communication device to the selected communication location selected, and
  use the radio network or multiple separate radio networks selected to transfer the image data to the central unit.

In addition, at least one embodiment of the invention concerns a computer program that can be directly loaded into a memory unit of a processing unit in a vehicle, especially an ambulance, the computer program comprising instructions for performing the steps of at least one embodiment of the inventive method when the program is executed on the processing unit. The processing unit can e.g. be implemented as part of the communication device or as part of a medical imaging device.

In addition, at least one embodiment of the invention concerns a memory of a processing unit in a vehicle, storing a computer program, the computer program including instructions for performing the method of an embodiment when the program is executed on the processing unit.

At least one embodiment of the invention also concerns a computer-readable storage medium containing electronically readable instructions comprising the computer program according to at least one embodiment of the present invention.

BRIEF DESCRIPTION OF THE DRAWINGS

Specific embodiments of the invention will be described in detail herein below with reference to the figures wherein the figures show schematically.

DETAILED DESCRIPTION OF THE EXAMPLE EMBODIMENTS

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without subdividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

Most of the aforementioned components, in particular the identification unit, can be implemented in full or in part in the form of software modules in a processor of a suitable control device or of a processing system. An implementation largely in software has the advantage that even control devices and/or processing systems already in use can be easily upgraded by a software update in order to work in the manner according to at least one embodiment of the invention.

At least one embodiment of the invention provides for providing image data to a central unit, comprising:

acquiring image data using a mobile imaging device, especially a mobile medical imaging device, that comprises or is connected to a mobile communication device, determining a bandwidth information that relates to a locally available bandwidth for a radio network or multiple separate radio networks, especially cellular networks, selecting a communication location for the mobile communication device (8) and/or selecting at least one of the radio networks based on the bandwidth information, and moving the mobile communication device to the selected communication location and/or using the selected radio network to transfer the image data to the central unit.

The solution is based on the idea that the locally available bandwidth is analyzed. Based on this analysis a suitable communication location or radio network is selected to transfer the image data to the central unit. The communication device can e.g. allow for a communication via several cellular networks, e.g. networks operated by different operators or providers.

Previous to the transfer of the image data, e.g. while acquiring the image data, the available bandwidth on the different networks can be checked. Alternatively the available bandwidth or an information that allows to predict the available bandwidth can be provided, e.g. in the form of map data, for the network or networks. This allows for the selection of the optimum network or a combination of networks to transfer the image data and therefore for a faster and/or more reliable data transfer. If information concerning the available bandwidth in the surrounding area is available, e.g. via the mentioned map data, a communication location that allows for a faster and/or more reliable data transfer can also be selected and the mobile communication device can be moved to that location previous to the data transfer.

In the cases of a mobile stroke unit the mobile communication device is typically part of the ambulance used to transport the patient to the hospital. In this case the selected communication location can e.g. be a location on the fastest route from the current location to the hospital. It can however also be advantageous to use a communication location that requires a slightly different route to the hospital or a detour. It can be advantageous to slightly delay the arrival of the patient in the hospital if this allows for an earlier treatment while the patient is still in the ambulance.

The central unit can allow access to the image data by a skilled person, e.g. a neuro radiologist, that can then extract information e.g. concerning the existence of blood clots, from images and communicate that information or a diagnosis determined from that information back to the communication device and therefore e.g. an ambulance transporting the patient. This especially allows for an early start of treatment in a mobile stroke unit.

The bandwidth information can be especially determined from location coded information, e.g. from map data. The current location of the mobile communication device, e.g. the location of an ambulance containing the mobile communication device, can be determined by a position determination system, e.g. a satellite positioning system like GPS. The bandwidth information concerning the available bandwidth at the current position of the mobile communication device and/or in other locations that might be used as communication locations can be extracted from location coded data and used. Alternatively or additionally it is possible to measure the bandwidth information. E.g. a signal-to-noise-ratio, round trip times, packet losses etc. can be determined for multiple radio networks and based on this data one or several of the radio networks can be selected to transfer the image data.

The mobile communication device can be a telemedicine system. It can allow for a connection to multiple radio networks, especially cellular networks. E.g. the communication device can provide multiple slots for sim cards and therefore allow a communication via multiple networks operated by multiple vendors. In the method according to the present invention the system can automatically decide which carrier or company can provide the highest bandwidth at the current location of the mobile communication device and therefore e.g. the mobile stroke unit. It can automatically use the radio network that provides the highest bandwidth. As will be discussed in more details later it is also possible to use multiple radio networks at the same time and e.g. split the image data between these information channels.

The bandwidth information can comprise a respective bandwidth value describing the locally available bandwidth or a factor influencing the locally available bandwidth for several locations for the radio network or for at least some of the radio networks, wherein one of these locations is selected as the communication location. It can therefore be determined that it might be advantageous to move the mobile communication device before initiating the image data transfer. It is e.g. possible to provide a driver of a mobile stroke unit with instructions how to reach the communication location. It is also possible to provide multiple bandwidth values for each location that each describe a respective factor influencing the local available bandwidth. E.g. a local signal-to-noise-ratio, round trip times for these locations and/or packet losses for the location can be provided for each network.

The communication location can be selected in such a way that a bandwidth condition is satisfied for the communication location, wherein the bandwidth condition is fulfilled for a location, if a predicted usable bandwidth for at least one of the radio networks or the sum of the predicted usable bandwidths for multiple radio networks for that location reaches or exceeds a threshold value, wherein the respective predicted usable bandwidth is determined from the bandwidth value for the respective location and radio network. It is possible that the bandwidth value directly provides the predicted usable bandwidth. It is however also possible to calculate the predicted usable bandwidth from one or multiple bandwidth values. While it is possible to use a fixed threshold value, it can be advantageous to adjust the threshold value. The threshold value can e.g. depend on a distance from the current location to the communication location or a predicted time to reach the communication location from the current location. It is also possible to first try and determine a communication location that satisfies a bandwidth condition using a first threshold value and then, if no suitable communication location can be found, repeat the process with a lower threshold value.

The communication location is preferably selected in such a way that a distance between the current location of the communication device and the communication location or a predicted time for reaching the communication location from the current location is minimized while the bandwidth condition is satisfied. This additional condition can ensure that the image data is transferred to the central unit as fast as possible. The time for reaching the communication location can be predicted by a navigation system that can also be used to a direct user to the communication location, e.g. a navigation system included in the ambulance of the mobile stroke unit. Methods for determining a route to a specific location and for predicting a time required for reaching this location are well known in the field of navigation systems and will therefore not be explained in detail.

The bandwidth information can be generated from or comprises map data for the radio network or at least one of the radio networks, describing a local distribution of the bandwidth value or of at least one parameter from which the bandwidth value is determined. The respective map data for a radio network can e.g. be provided by the operator of the respective network or by a third party that is monitoring available bandwidth in a certain network. The bandwidth information, especially the map data, can be automatically updated. The communication device or a further unit connected to the communication device can request updates from a provider, e.g. the operator of the respective network or the third party. It can e.g. check for updates after certain time intervals, e.g. a certain number of hours or days. Alternatively or additionally it is possible to push updated bandwidth information, especially map data, from a provider to the mobile communication device, if the respective information changes.

The image data can be split into at least two separate datasets that are transmitted to the central unit via different radio networks. This can further improve the speed of a transfer of the image data to the central unit. The communication device can e.g. allow for multiple parallel connections to different radio networks, especially to different cellular networks. By using multiple radio networks in parallel their available bandwidth can effectively be added.

The relative size of the separate datasets can be determined in dependence of the predicted available bandwidths of the radio networks used to transmit the datasets. The relative size of the separate datasets can especially be determined in such a way that a predicted transmission time to transmit the respective separate dataset on the respective radio network is approximately the same for all of the separate datasets. This is equivalent to minimizing the overall time required to transmit the image data over a given subset of the radio networks.

The communication unit can be installed in a vehicle, especially in an ambulance. That vehicle can be a motor vehicle. Preferably the imaging device is also installed in the vehicle. The vehicle can especially be a mobile stroke unit.

The step of moving the communication device can comprise the use of an output device of the communication device or the vehicle to output navigation information concerning a navigation to the communication location for a driver of the vehicle. E.g. the vehicle can comprise a navigation system for providing navigation information to a driver of the vehicle, wherein the communication location can be automatically programmed into the navigation system as a target location after it is selected. The driver can then be guided to the communication location via the navigation system. The navigation information can be optical information, e.g. a map showing the route to the communication location can be displayed. Additionally or alternatively acoustic navigation information can be used, e.g. voice instructions can be provided.

To simplify the operation of the vehicle for the driver a navigation system or the communication device can provide a simple to use element, e.g. a button that can be pressed, that automatically triggers the navigation to the communication location.

For example the driver of the vehicle can push a button of the navigation system or the communication device or perform some other simple user input to trigger the steps of checking for available radio networks, e.g. networks operated by different carriers and/or companies, using a bandwidth information available for the different radio networks, e.g. map data concerning the bandwidth value for different networks, and providing directions to the driver to the communication location, e.g. the closest spot which reaches a previously defined threshold of lowest acceptable transmission speed within a certain maximum distance.

The transfer of the image data to the central unit can be automatically started once the communication location is reached or approached. The transfer of the image data to the central unit can e.g. automatically start once the distance to the communication location drops blow a certain threshold, e.g. 20 m or 5 m.

Preferably the imaging device is a computer tomography scanner. Computer tomography scanners can especially be used to check for the existence of blood clots and/or the location of these blood clot(s) in the brain area and are therefore useful for determining whether a patient suffered from a stroke.

In addition to the inventive method, at least one embodiment of the invention concerns a vehicle, especially an ambulance, comprising an imaging device, especially a medical imaging device, and a communication device, wherein the vehicle is configured to perform at least one embodiment of the inventive method. The vehicle can especially be a mobile stroke unit.

In addition, at least one embodiment of the invention concerns a computer program that can be directly loaded into a memory unit of a processing unit in a vehicle, especially an ambulance, the computer program comprising instructions for performing the steps of at least one embodiment of the inventive method when the program is executed on the processing unit. The processing unit can e.g. be implemented as part of the communication device or as part of a medical imaging device.

At least one embodiment of the invention also concerns a computer-readable storage medium containing electronically readable instructions comprising the computer program according to at least one embodiment of the present invention.

Figure 1:
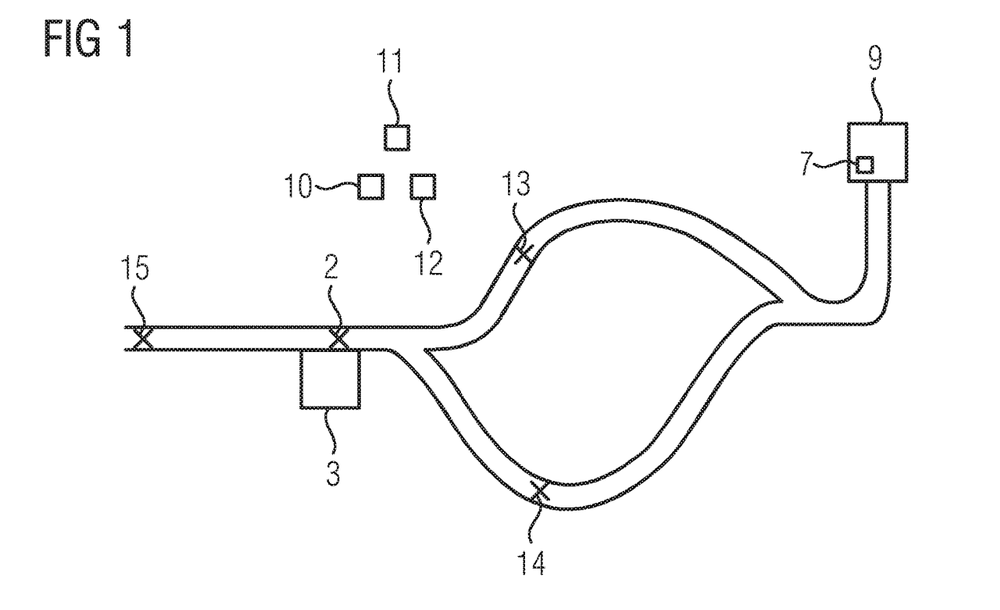
FIG. 1 a situation in which an embodiment of the inventive method is used to transfer image data to a central unit, and FIG. 2 an embodiment of a vehicle according to the present invention.
Figure 2:
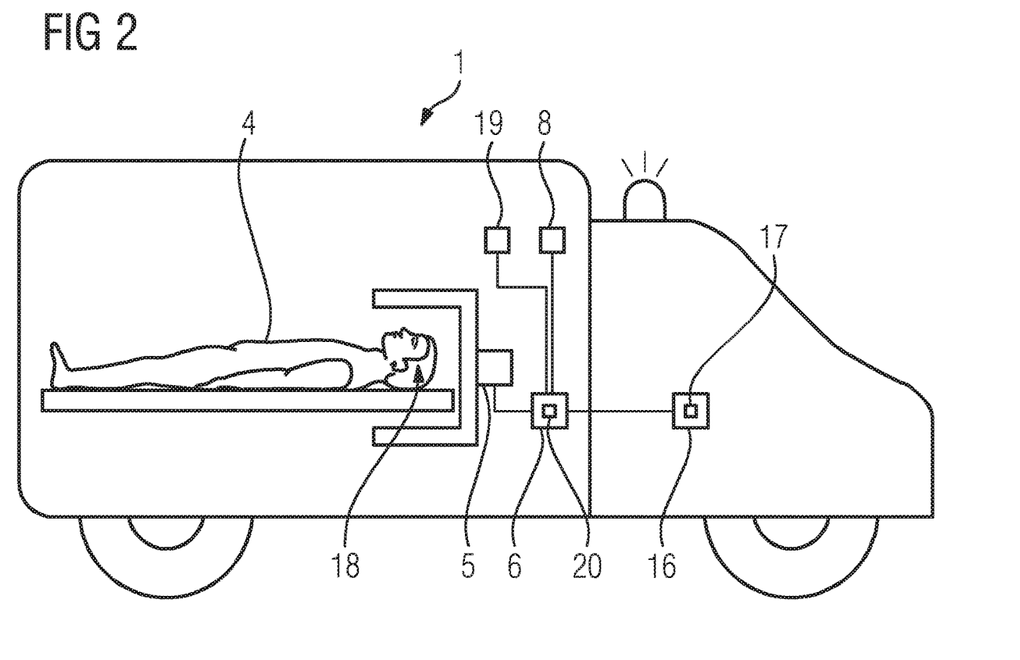

FIG. 1 shows a situation in which a method for providing image data to a central unit 7 is used. In the example the method is used to transfer medical image data from a mobile stroke unit, the vehicle 1 that is shown in FIG. 2, to a central unit 7 in a hub, e.g. a hospital 9, for the purpose of determining, whether a patient 4 suffered a stroke and/or the location of a blood clot and should therefore be treated for such. The central unit can be located in the hospital 9 that the patient is transported to. It is however also possible to use a central unit 7 located in some other hub, e.g. a computer center hosting one or several experts.

When an ambulance is called to a house 3, the vehicle 1 is typically parked in close proximity to the house 3, e.g. at the location 2. The patient 4 is moved to the vehicle 1 and medical image data is acquired by the mobile imaging device 5. In the example the mobile imaging device 5 is a computed tomography scanner that is used to acquire three-dimensional image data concerning the head 18 of the patient 4. A specialist in the hub can analyse this data and determine if the patient 4 suffered from a stroke or if his symptoms are caused by a different medical problem and/or determine the type of stroke the patient suffered and/or the location of blood cots. If the problems are caused by a stroke, treatment can immediately be started while the patient is still transported to the hospital 9 in the vehicle 1. This allows for an earlier start of the treatment which is advantageous in the case of a stroke.

The acquired image data is transferred to a processing unit 6 of the vehicle 1. The processing unit 6 is shown as a separate component but could also be integrated into the imaging device 5, the communication device 8 or the navigation system 16 or some other component of the vehicle 1. The image data is then to be sent to the central unit 7 via the mobile communication device 8. The vehicle 1 is designed specifically to support a sufficiently fast transfer of the image data to the central unit 7. To achieve this, bandwidth information that relates to a locally available bandwidth for multiple separate radio network, especially cellular networks, is analysed. The different networks can be operated by different companies and are schematically represented in FIG. 1 by respective base stations 10, 11, 12. The different networks can provide locally different coverage and bandwidth. It is e.g. possible that at the location 2 one of the networks would provide a high bandwidth, another one a low bandwidth and a third does not provide any connection at all. By analysing the bandwidth information the radio network used for the transfer of the image data to the central unit 7 can be selected.

It is also possible to select a communication location at which the transfer is performed. This is advantageous when the expected bandwidth for one or multiple of the networks is rather low at the location 2 and it would therefore be advantageous to first move the vehicle 1 and therefore the mobile communication device 8 to a different location, e.g. to the communication location 13, 14 or 15, before transferring the image data to the central unit 7. Both approaches will be discussed in detail below.

Preferably the bandwidth information for each network comprises bandwidth values that directly describe the locally available bandwidth or at least one factor influencing the locally available bandwidth for several locations. Especially map data that describes the bandwidth or the factors influencing the bandwidth can be provided, e.g. by the respective operators of the networks. This respective data can e.g. be updated at regular intervals by downloading updated map data from the respective provider.

The processing unit 6 determines the current location 2 of the vehicle 1 via the location determining device 19, e.g. a GPS-receiver. Based on this location and the previously discussed map data the bandwidth values for the surrounding areas are known for each of the networks. The communication location can therefore be selected in such a way that a bandwidth condition is satisfied for the communication location, wherein the bandwidth condition is fulfilled for a location 2, 13, 14, 15, if a predicted useable bandwidth for at least one of the radio networks for that location reaches or exceeds a threshold value. A predicted useable bandwidth can be directly given by the map data or determined from the bandwidth value or values provided by the map data.

To ensure that the image data is transmitted to the central unit 7 as soon as possible a distance between the current location 2 of the vehicle 1 and therefore the communication device 8 and the communication location 13, 14, 15 or a predicted time for reaching the communication location 13, 14, 15 from the current location 2 can be minimized under the condition that the previously discussed bandwidth condition is satisfied. Once the optimum communication location 13, 14, 15 is determined and reached the transfer of the image data can automatically be started. Preferably the network that allows for the highest bandwidth at the communication location is used to transfer the image data to the central unit 7.

In an alternate embodiment it would also be possible to use multiple networks in parallel to transmit the image data to the central unit 7. In this case the bandwidth condition can be fulfilled for a location, if the sum of the predicted useable bandwidths for multiple radio networks for that location reaches or exceeds the threshold value. The image data can then be split into at least two separate datasets that are transmitted to the central unit 7 by different radio networks. The relative size of the separate datasets can be determined in dependence of the predicted available bandwidths of the used radio networks. E.g. a smaller portion of the data can be transferred via a slower network via the larger part of the data is transferred via a faster network.

To assist a driver of the vehicle 1 in reaching the selected communication location 13, 14, 15 an output device 17 of the vehicle 1 that is especially part of a navigation system 16, can be used to output navigation information concerning a navigation to the communication location 13, 14, 15. While the driver is guided to the communication location 13, 14, 15 the current position of the vehicle 1 can be determined via the location determination device 19 and the transfer of the image data can automatically be started once the communication location 13, 14, 15 is reached or approached.

The previously discussed steps can be implemented via a computer program that can be directly loaded into a memory unit 20 of the processing unit 6 of the vehicle 1. The computer program can be provided in the shape of a non-transitory computer-readable storage medium (not shown).

Although the present invention has been described in detail with reference to the preferred embodiment, the present invention is not limited by the disclosed examples from which the skilled person is able to derive other variations without departing from the scope of the invention.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for providing medical image data from a vehicle including a medical imaging device to a central unit, comprising:
   acquiring the medical image data using the medical imaging device, the medical imaging device being a mobile communication device or being connected to a mobile communication device;
   determining bandwidth information relating to locally available bandwidths for radio networks prior to transfer of the medical image data;
   selecting at least one communication network from the radio networks currently available to the mobile communication device having the highest bandwidth available;
   selecting a communication location for transfer of the medical image data from the mobile communication device based on the bandwidth information determined prior to transfer of the medical image data,
   moving the mobile communication device to the selected communication location selected having the highest bandwidth available, and
   using the radio network or multiple separate radio networks selected to transfer the medical image data from the mobile communication device to the central unit.

2. The method of claim 1, wherein the bandwidth information includes a respective bandwidth value describing a locally available bandwidth or a factor influencing the locally available bandwidth for several locations for the radio network or at least one of the radio networks, and wherein one of the several locations is selected as the communication location.

3. The method of claim 2, wherein the communication location is selected such that a bandwidth condition is satisfied for the communication location, wherein the bandwidth condition is fulfilled for a location upon a predicted usable bandwidth for at least one of the radio networks or a sum of predicted usable bandwidths for multiple radio networks for the location reaching or exceeding a threshold value, and wherein the predicted usable bandwidth is determined from the bandwidth value for the location and the at least one radio network.

4. The method of claim 3, wherein the bandwidth information is generated from, or includes, map data for the radio network or at least one of the radio networks, describing a local distribution of the bandwidth value or of at least one parameter from which the bandwidth value is determined.

5. The method of claim 3, wherein the communication location is selected such that a distance between a current location of the communication device and a communication location or a predicted time for reaching the communication location from a current location is minimized while the bandwidth condition is satisfied.

6. The method of claim 5, wherein the bandwidth information is generated from, or includes, map data for the radio network or at least one of the radio networks, describing a local distribution of the bandwidth value or of at least one parameter from which the bandwidth value is determined.

7. The method of claim 2, wherein the bandwidth information is generated from, or includes, map data for the radio network or at least one of the radio networks, describing a local distribution of the bandwidth value or of at least one parameter from which the bandwidth value is determined.

8. The method of claim 1, wherein the image date is split into at least two separate datasets that are transmitted to the central unit via different radio networks.

9. The method of claim 8, wherein a relative size of the at least two separate datasets is determined in dependence of predicted available bandwidths of respective radio networks used to transmit the at least two separate datasets.

10. The method of claim 1, wherein the mobile communication device is installable in a vehicle.

11. The method of claim 10, wherein the moving of the mobile communication device includes using at least one of an output device of the mobile communication device or the vehicle to output navigation information concerning a navigation to the communication location for a driver of the vehicle.

12. The method of claim 1, wherein the transfer of the image data to the central unit is automatically started once the communication location is reached or approached.

13. The method of claim 1, wherein the medical imaging device is a computed tomography scanner.

14. The method of claim 1, wherein the acquiring of the image data is achieved using a mobile medical imaging device.

15. The method of claim 1, wherein the mobile communication device is installable in an ambulance.

16. The method of claim 15, wherein the moving of the communication device includes using at least one of an output device of the communication device or the ambulance to output navigation information concerning a navigation to the communication location for a driver of the ambulance.

17. A vehicle, comprising:
a medical imaging device configured to acquire medical image data, the medical imaging device being a mobile communication device or being connected to a mobile communication device; and
a communication device, configured to
    determine bandwidth information relating to locally available bandwidths for radio networks prior to transfer of the medical image data from the mobile communication device;
    select at least one communication network from the radio networks currently available to the mobile communication device having the highest bandwidth available;
    select a communication location for the mobile communication device based on the bandwidth information determined prior to transfer of the medical image data, and
    move the mobile communication device to the selected communication location selected having the highest bandwidth available prior to transfer of the medical image data, and
    use the radio network or multiple separate radio networks selected to transfer the medical image data from the mobile communication device to a central unit.

18. A memory of a processing unit in a vehicle, storing a computer program, the computer program including instructions for performing the method of claim 1 when the program is executed on the processing unit.

19. A non-transitory computer-readable storage medium containing electronically readable instructions of a computer program, the computer program including instructions for performing the method of claim 1 when the program is executed on by a processor.

* * * * *